(12) United States Patent
Witker et al.

(10) Patent No.: US 8,564,871 B2
(45) Date of Patent: Oct. 22, 2013

(54) ELECTROCHROMIC COMPOSITION, A METHOD OF FORMING THE ELECTROCHROMIC COMPOSITION AND AN ELECTROCHROMIC APPARATUS

(75) Inventors: David Witker, Bay City, MI (US); Toshio Suzuki, Houston, TX (US)

(73) Assignee: Dow Corning Corporation, Midland, MI (US)

( * ) Notice: Subject to any disclaimer, the term of this patent is extended or adjusted under 35 U.S.C. 154(b) by 500 days.

(21) Appl. No.: 12/812,309

(22) PCT Filed: Jan. 8, 2009

(86) PCT No.: PCT/US2009/000109
§ 371 (c)(1),
(2), (4) Date: Jul. 9, 2010

(87) PCT Pub. No.: WO2009/089031
PCT Pub. Date: Jul. 16, 2009

(65) Prior Publication Data
US 2010/0284053 A1    Nov. 11, 2010

Related U.S. Application Data

(60) Provisional application No. 61/020,630, filed on Jan. 11, 2008.

(51) Int. Cl.
*G02F 1/153* (2006.01)
*G02B 5/23* (2006.01)

(52) U.S. Cl.
USPC .......... 359/270; 359/265; 359/266; 359/267; 359/268; 359/269; 359/271; 359/272; 359/273; 359/274; 359/275; 252/586

(58) Field of Classification Search
USPC .................... 359/265–275; 252/586
See application file for complete search history.

(56) References Cited

U.S. PATENT DOCUMENTS

| | | | |
|---|---|---|---|
| 2,901,460 | A | 8/1959 | Boldebuck |
| 3,957,725 | A | 5/1976 | Limburg |

(Continued)

FOREIGN PATENT DOCUMENTS

| | | |
|---|---|---|
| EP | 0771805 A1 | 5/1997 |
| WO | WO 95/01871 A1 | 1/1995 |

(Continued)

OTHER PUBLICATIONS

Bartlett et al; "Characterization and application of carbazole modified polysiloxanes to electrochromic displays," by Bartlett et al, Journal of Non-Crystalline Solids, vol. 198-200(1996), pp. 665-668).*

(Continued)

*Primary Examiner* — Evelyn A. Lester
(74) *Attorney, Agent, or Firm* — Howard & Howard Attorneys PLLC

(57) ABSTRACT

An electrochromic apparatus comprises a first electrode layer and a second electrode layer spaced from and disposed substantially parallel to the first electrode. An electrochromic layer is disposed between the first and second electrode layers. An electrolyte layer is disposed between the electrochromic layer and one of the electrode layers. The electrochromic layer comprises the dehydration reaction product of a hydrolyzed aromatic component. An electrochromic composition comprises an aromatic component having an aromatic core and at least two silicon-based groups pending from the aromatic core. The silicon-based groups have a silicon-bonded group selected from the group of hydrolyzable groups, hydrolyzates of hydrolyzable groups, and combinations thereof. The thickness of the electrochromic layer may be minimized while achieving desirable electrochromic properties that are typically characteristic of thicker electrochromic layers, thereby imparting the electrochromic apparatus with excellent versatility and flexibility.

25 Claims, 3 Drawing Sheets

(56) References Cited

U.S. PATENT DOCUMENTS

| | | |
|---|---|---|
| 4,933,053 A | 6/1990 | Tieke |
| 5,391,638 A | 2/1995 | Katsoulis et al. |
| 5,712,360 A | 1/1998 | Kobayashi et al. |
| 6,517,958 B1 | 2/2003 | Sellinger et al. |
| 2003/0129451 A1 | 7/2003 | Nukada et al. |
| 2005/0205860 A1 | 9/2005 | Hsu et al. |
| 2005/0209388 A1 | 9/2005 | Hsu et al. |
| 2005/0222333 A1 | 10/2005 | Hsu |
| 2005/0224765 A1 | 10/2005 | Hsu et al. |
| 2005/0224788 A1 | 10/2005 | Hsu et al. |
| 2005/0227081 A1 | 10/2005 | Hsu et al. |
| 2006/0202166 A1 | 9/2006 | Suzuki et al. |
| 2006/0209382 A1 | 9/2006 | Lin et al. |

FOREIGN PATENT DOCUMENTS

| | | |
|---|---|---|
| WO | WO 2005/037955 A1 | 4/2005 |
| WO | WO 2006/085319 A2 | 8/2006 |

OTHER PUBLICATIONS

PCT International Search Report for PCT/US2009/000109, dated Apr. 7, 2009, 4 pages.

* cited by examiner

ELECTROCHROMIC COMPOSITION, A METHOD OF FORMING THE ELECTROCHROMIC COMPOSITION AND AN ELECTROCHROMIC APPARATUS

RELATED APPLICATIONS

This application claims priority to and all the advantages of International Patent Application No. PCT/US2009/000109, filed on Jan. 8, 2009, which claims priority to U.S. Provisional Patent Application No. 61/020,630, filed on Jan. 11, 2008.

FIELD OF THE INVENTION

The present invention generally relates to an electrochromic composition and, more specifically, to an electrochromic composition that includes an aromatic component having a silicon-based substituent.

DESCRIPTION OF THE RELATED ART

Electrochromic compositions are known and are typically utilized in an electrochromic apparatus to form an electrochromic layer. The electrochromic apparatus typically comprises the electrochromic layer, an electrolyte layer, and first and second electrode layers. The first and second electrode layers are spaced from and disposed substantially parallel to one another. The electrochromic layer is disposed between the first and second electrode layers. The electrolyte layer is disposed between the electrochromic layer and one of the electrode layers.

Typically, the electrochromic apparatus further comprises first and second substrate layers; the first and second substrate layers are typically glass, e.g. to form an electrochromic window. Additional examples of electrochromic apparatuses include: an indoor and outdoor display, an electronic data display, a mirror, a clock, a sun roof, a shade band, a monitor, a security or privacy partition, a solar panel, a sky light and an information display.

The electrochromic apparatus is activated by applying a voltage across the first and second electrode layers. When the voltage is applied across the first and second electrode layers, an electric field is generated within the electrochromic layer. The electric field induces an electrochromic effect in the electrochromic layer, thereby resulting in a change in light transmission properties of the electrochromic layer, e.g. from transparent to opaque or tinted. The change in the light transmission properties of the electrochromic layer typically lasts for a period of time, though the change in the light transmission properties of the electrochromic layer can be reversed by reversing the polarity of the voltage. Several different types of electrochromic layers are typically utilized. However, the principal types of electrochromic layers are inorganic thin films, organic polymer films, and organic solutions.

The degree of change in light transmission properties of the electrochromic layer is dependent on various factors. For example, thickness of the electrochromic layer is one factor that has an effect on the degree of change in light transmission properties of the electrochromic layer, with thicker electrochromic layers generally capable of more pronounced electrochromic effects than thinner electrochromic layers. However, thickness of the electrochromic layer is inversely proportional to flexibility and versatility of the electrochromic layer and, by extension, flexibility and versatility of an electrochromic apparatus that includes the electrochromic layer, with thinner electrochromic layers allowing greater flexibility and versatility of the electrochromic apparatus. Therefore, it would be advantageous to minimize the thickness of the electrochromic layer while substantially maintaining comparable electrochromic properties characteristic of thicker electrochromic layers.

The change in light transmission properties of the electrochromic layer is typically limited to the inherent properties of the electrochromic layer, e.g. the opaque or tinted effect is limited to a particular color. In some applications, it may be desirable to have the particular color different from the particular color provided by existing electrochromic layers. Therefore, it would be advantageous to provide the electrochromic layer such that the particular color exhibited by the change in light transmission properties is customizable based on the aromatic groups present in the electrochromic layer, e.g. the particular color is customizable for a particular application of the electrochromic apparatus.

Accordingly, it would be advantageous to provide an electrochromic composition that is suitable to form an electrochromic layer while contemporaneously minimizing a thickness of the electrochromic layer that is required to achieve a desired change in light transmission properties of the electrochromic layer. In addition, it would be advantageous to provide a reaction mechanism to form the electrochromic composition.

SUMMARY OF THE INVENTION AND ADVANTAGES

The present invention provides an electrochromic apparatus comprising a first electrode layer and second electrode layer spaced from and disposed substantially parallel to the first electrode layer. An electrochromic layer is disposed between the first and second electrode layers. The electrochromic layer comprises the dehydration reaction product of a hydrolyzed aromatic component having an aromatic core and at least two silicon-based substituents pending from the aromatic core. The silicon-based substituents have a silicon-bonded hydrolyzate of a hydrolyzable group. An electrolyte layer is disposed between the electrochromic layer and one of the electrode layers.

The present invention further provides an electrochromic composition. The electrochromic composition comprises an aromatic component having an aromatic core and at least two silicon-based substituents pending from the aromatic core. The silicon-based substituents have a silicon-bonded group selected from the group of hydrolyzable groups, a hydrolyzate of a hydrolyzable group, and combinations thereof.

The present invention further provides a method of forming the electrochromic composition comprising the steps of providing an aromatic group and bonding at least two silicon-based substituents to the aromatic group.

The electrochromic composition, and the electrochromic layer that comprises the dehydration reaction product of the hydrolyzed aromatic component, have excellent electrochromic properties. In addition, the thickness of the electrochromic layer may be minimized while achieving desirable electrochromic properties that are typically characteristic of thicker electrochromic layers, thereby imparting the electrochromic apparatus with excellent versatility and flexibility. In particular, by including two of the specific types of silicon-based substituents in the aromatic component, the resulting dehydration reaction product includes aromatic groups that are incorporated into a resulting polymer chain, thereby maximizing a density of aromatic groups present in the electrochromic layer. Aromatic groups are responsible for the electrochromic properties of the electrochromic layer.

Because the density of aromatic groups in the electrochromic layer is maximized, the thickness of the electrochromic layer may be minimized while still achieving desirable electrochromic properties that are typically characteristic of thicker electrochromic layers. Further, a particular color resulting from a change in light transmission properties of the electrochromic layer may be customized based on the aromatic groups present in the electrochromic layer, e.g. the particular color may customized for a particular application of the electrochromic apparatus.

BRIEF DESCRIPTION OF THE DRAWINGS

Other advantages and aspects of this invention may be described in the following detailed description when considered in connection with the accompanying drawings wherein.

DETAILED DESCRIPTION OF THE INVENTION

An electrochromic apparatus is provided. The electrochromic apparatus may be used for applications including, but not limited to, indoor and outdoor displays, electronic data displays, mirrors, clocks, sun roofs, shade bands, monitors, security or privacy partitions, solar panels, sky lights, windows, and information displays.

Figure 1:
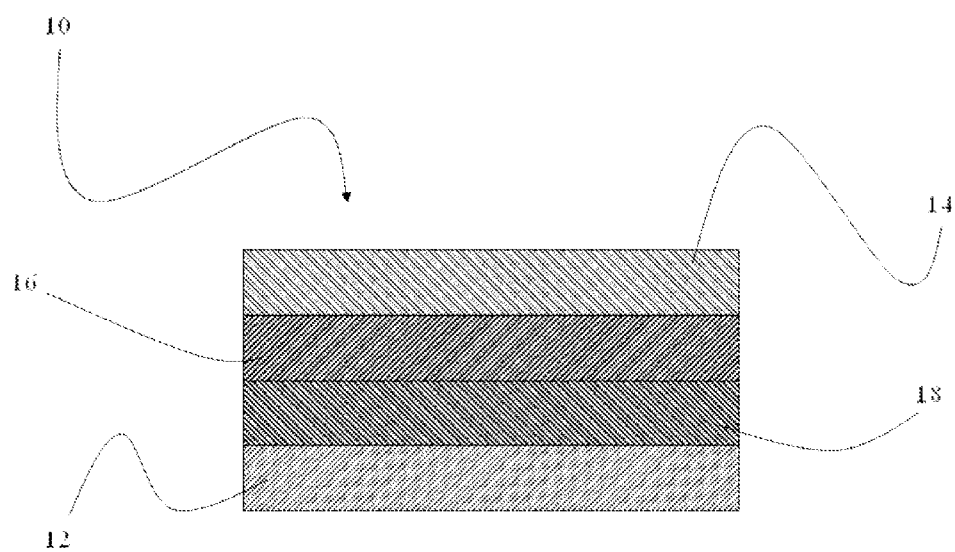
FIG. 1 is a schematic cross-sectional view of one embodiment of an electrochromic apparatus including first and second electrode layers, an electrochromic layer, and an electrolyte layer.
Figure 2:
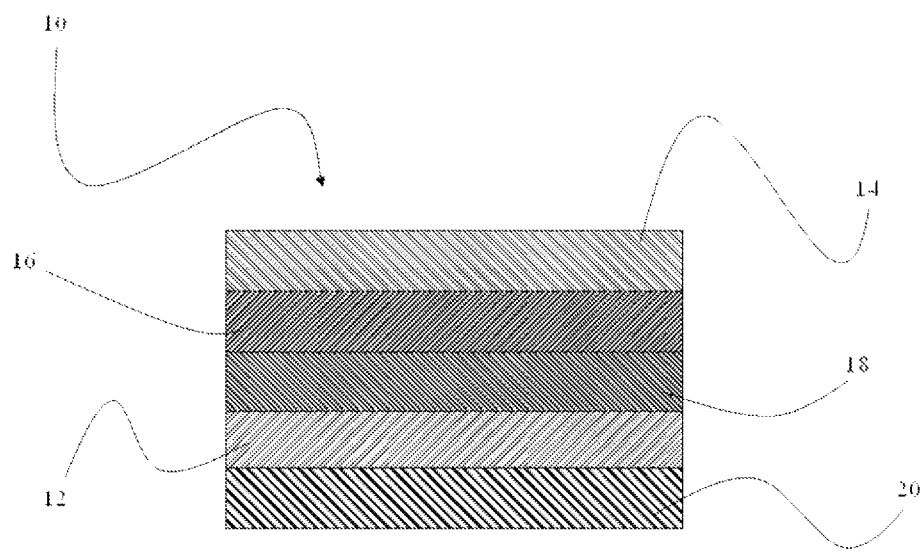
FIG. 2 is a schematic cross-sectional view of another embodiment of an electrochromic apparatus including first and second electrode layers, an electrochromic layer, an electrolyte layer, and a first substrate layer.
Figure 3:
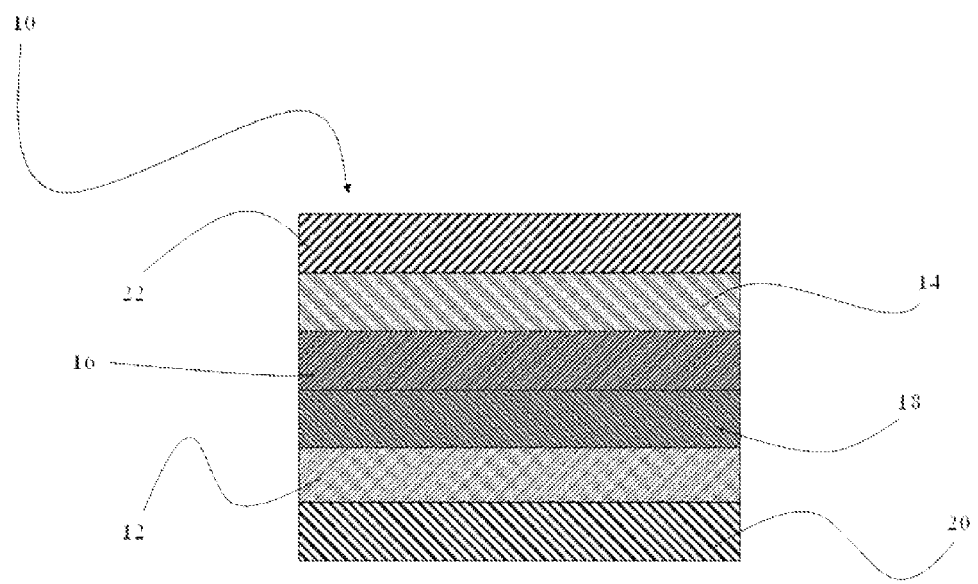
FIG. 3 is a schematic cross-sectional view of yet another embodiment of an electrochromic apparatus including first and second electrode layers, an electrochromic layer, an electrolyte layer, and first and second substrate layers.

The electrochromic apparatus 10 comprises a first electrode layer 12 and second electrode layer 14 that is spaced from and disposed substantially parallel to the first electrode layer 12. An electrochromic layer 16 is disposed between the first and second electrode layers 12, 14. An electrolyte layer 18 is disposed between the electrochromic layer 16 and the first electrode layer 12. For example, as shown in FIG. 1, the electrochromic apparatus 10 comprises the first electrode layer 12, the second electrode layer 14 spaced from the first electrode layer 12, the electrochromic layer 16 disposed between the first and second electrode layers 12, 14, and the electrolyte layer 18 disposed between the first electrode layer 12 and the electrochromic layer 16. Typically, the electrochromic apparatus 10 further comprises a first substrate layer that is disposed on an exterior surface of one of the electrode layers, on an opposite side of the subject electrode layer from the electrolyte layer or electrochromic layer, depending upon the specific electrode layer. For example, as shown in FIG. 2, the electrochromic apparatus 10 may include the first substrate layer 20 disposed on the exterior surface of the first electrode layer 12 on the opposite side of the first electrode layer 12 from the electrolyte layer 18. The electrochromic apparatus 10 also typically comprises a second substrate layer that is disposed on an exterior surface of the other of the electrode layers. For example, as shown in FIG. 3, the electrochromic apparatus 10 may include the second substrate layer 22 disposed on the exterior surface of the second electrode layer 14 on the opposite side of the second electrode layer 14 from the electrochromic layer 16. Stated differently, the electrochromic apparatus 10 typically comprises the first and second substrate layers 20 22 that encapsulate the functional portions of the electrochromic apparatus 10, such as the electrode layers 12 14, electrolyte layer 18, and electrochromic layer 16. By encapsulating the functional portions of the electrochromic apparatus 10, the first and second substrate layers 20, 22 typically provide support for the first and second electrode layers 12, 14 and prevent degradation of the electrochromic apparatus 10 by shielding the electrochromic apparatus 10 from natural elements.

To activate the electrochromic apparatus, a voltage is applied across the first and second electrode layers. The voltage generates an electric field within the electrochromic layer. The electric field induces an electrochromic effect in the electrochromic layer, thereby resulting in a change in light transmission properties of the electrochromic layer, e.g. from transparent to opaque or tinted. The corresponding change in light transmission properties may last for a period of time after removal of the voltage; however, the change in light transmission properties may be reversed to the transparent state upon a reversal in the polarity of the voltage.

The first and second substrate layers may comprise any substantially transparent material including, but not limited to, glass, polyvinyl chloride, polyethylene, polycarbonate, polyethylene terephthalate, or any polymeric, ceramic, or other material known in the art to be substantially transparent. As used throughout the instant application, the term "substantially transparent" means transmittance of visible light is greater than 70%. In one embodiment of the present invention, the first and second substrate layers comprise glass. The thickness of the first and second substrate layers may vary depending upon the particular application for which the electrochromic apparatus is meant. However, typical thicknesses for the first and second substrate layers are from about 0.5 to about 10 millimeters.

In one embodiment of the present invention, the first and second electrodes each comprise indium tin oxide (ITO). ITO is a mixture of indium(III) oxide and tin (IV) oxide. The ITO may be deposited on the first and/or second substrate layers by electron beam evaporation, physical vapor deposition, sputter deposition techniques, or any other techniques known by those skilled in the art to form the electrode layers. Alternatively, in another embodiment, the first and second electrode layers may comprise conductive carbon nanotubes, aluminum-doped zinc oxide, indium(III) oxide, tin(IV) oxide, antimony tin oxide, fluorine-doped tin oxide, iridium tin oxide or any other substantially transparent material known in the art that is capable of conducting electricity, which may be deposited on the first and/or second substrate layers through methods that are known in the art. Typical thicknesses for the first and second electrode layers are from about 10 to about 50 nanometers, more typically from about 100 to about 300 nanometers.

The electrolyte layer of the electrochromic apparatus may be any suitable material comprising free ions in an electrically conductive medium. In one embodiment, the electrolyte layer is a gelatinous material. Typically, electrolyte layers that are gelatinous or solid materials comprise a polymer matrix, a solvent carrier, and a source of ions. The polymer matrix may be any suitable polymer matrix, e.g. polyvinyl chloride, and the source of ions may be any suitable source of ions, e.g. lithium perchlorate ($LiCl_4$). It should be appreciated that the electrolyte layer may also comprise a solid material or, alternatively, a liquid material. In one embodiment of the present invention, the electrolyte layer is a liquid electrolyte. The liquid electrolyte is capable of penetrating the electrochromic layer, thereby allowing a substantially instantaneous inducement of the electrochromic effect in the electrochromic layer upon the application of the voltage. While liquid electrolyte layers may excessively degrade known electrochromic layers, the electrochromic layer of the present invention maintains sufficient durability even when the liquid electrolyte is used, which is a distinct advantage of the electrochromic layers of the present invention. The liquid electrolyte may be any conductive liquid known in the art. The electrolyte layer may be formed through methods that are known in the art. Typical thicknesses for the electrolyte layer are from about 100 to about 2000 micrometers, more typically from about 500 to 1000 micrometers.

The electrochromic layer comprises the dehydration reaction product of a hydrolyzed aromatic component that has an aromatic core and at least two silicon-based substituents that pend from the aromatic core. The silicon-based substituents each have a silicon-bonded hydrolyzable group that enables the dehydration reaction to occur, thereby resulting in a solid polysiloxane that is described in further detail below.

The electrochromic layer is, more specifically, formed from an electrochromic composition that comprises an aromatic component. The aromatic component comprises an aromatic core having at least two silicon-based substituents pending from the aromatic core. The silicone-based substituents each have a silicon-bonded group selected from the group of hydrolyzable groups, hydrolyzates of hydrolyzable groups, and combinations thereof. When the silicon-bonded groups are all hydrolyzates of hydrolyzable groups, the aromatic component is the same as the hydrolyzed aromatic component described above that is subjected to the dehydration reaction to produce the electrochromic layer. While it is readily appreciated that the hydrolyzable groups are generally hydrolyzed to enable the dehydration reaction, the electrochromic composition may, in the context of the instant invention, be provided prior to such hydrolysis of the hydrolyzable groups or subsequent to such hydrolysis and the present invention is not limited to the state of hydrolysis of the hydrolyzable groups.

The aromatic core, by having at least two silicon-based substituents, effectively incorporates aromatic functionality into the polysiloxane chain, as opposed to merely including aromatic functionality pending from the polysiloxane chain. As such, the density of aromatic functionality present in the polysiloxane that results from the dehydration reaction is maximized, thereby maximizing the electrochromic properties of the electrochromic layer that comprises the dehydration reaction product of the hydrolyzed aromatic component.

In one embodiment, the aromatic core may solely comprise carbon and hydrogen atoms. Alternatively, in another embodiment, the aromatic core may be an aromatic amine, an aromatic ether, or an aromatic thiol. In the aromatic amines, ethers, and thiols, a nitrogen, oxygen, or sulphur-based group, respectively, may be bonded within a cyclical portion of the core. The cyclical portion, as used herein, is a portion of the aromatic core that includes one or more aromatic rings. When the cyclical portion includes more than one aromatic ring, the cyclical portion may be characterized as a polyaromatic component and, thus, the aromatic component comprises the polyaromatic component. The rings in the cyclical portion including more than one aromatic ring may share a common carbon-carbon bond, or may be joined through other non-aromatic ring structures. The nitrogen, oxygen, or sulphur-based group may be integral within the cyclical portion, i.e., the nitrogen, oxygen, or sulphur-based group may be incorporated into one of the rings in the cyclical portion. Alternatively, the nitrogen, oxygen, or sulphur-based group may reside outside of the cyclical portion of the core. For example, the nitrogen-based group may be situated between two different cyclical portions that are part of the aromatic core, in which case the aromatic core may be characterized as a polyaromatic component. It is to be appreciated that the electrochromic composition may include combinations of aromatic components having different types of aromatic cores.

As set forth above, the aromatic core has at least two silicon-based substituents pending therefrom. In one embodiment, the silicon-based substituents are bonded on opposite sides of the aromatic core so as to minimize steric hindrance. In another embodiment, three or more silicon-based substituents are bonded to the aromatic core. When three or more silicon-based substituents are bonded to the aromatic core, the three or more silicon-based substituents are typically bonded such that the distance between each of the silicon-based substituents is approximately the same, thereby maximizing a potential for excellent cross-linking ability while reducing steric hindrance. Inclusion of three or more silicon-based substituents is one way that potential for excellent cross-linking ability is imparted to the electrochromic composition. Excellent cross-linking in the resulting electrochromic layer renders the electrochromic layer more insoluble and durable than electrochromic layers that are uncross-linked or that have minimal cross-linking. Insolubility and durability of the electrochromic layer contribute to overall robustness of the electrochromic apparatus. Notwithstanding the above, it is to be appreciated that the instant invention is not limited to electrochromic compositions that are capable of cross-linking.

In one embodiment, the silicon based substituent is of the general structure (I):

wherein X is selected from the group of hydrolyzable groups, hydrolyzates of a hydrolyzable group, and combinations thereof; Y is selected from the group of X, monovalent aliphatic $C_1$ to $C_{10}$ groups, phenyl groups, and combinations thereof; and R is a divalent aliphatic group having from 0 to 10 carbon atoms, wherein R is bonded to the aromatic core. It should be appreciated that R is optional and that the silicon atom may be directly bonded to the aromatic core. Alternatively, the silicon atom may be bonded to the aromatic core through R. Alternatively still, the silicon atom may be bonded to the aromatic core through both R and through another linking atom, such as an oxygen atoms, nitrogen atom, etc., which linking atom is bonded to the aromatic core.

While it is to be appreciated that any hydrolyzable group may be suitable for X, examples of suitable hydrolyzable groups include, but are not limited to, hydride groups, halogen atoms, hydroxyl groups, alkoxy groups, acyloxy groups, ketoxymate groups, amide groups, acid amide groups, and aminoxy groups. Examples of suitable hydrolyzates include hydrolyzates of any of the aforementioned hydrolyzable groups. It should be appreciated that, although there may be only one hydrolyzable group or hydrolyzate of a hydrolyzable group in a given silicon-based substituent, the phrase "combinations thereof" is appropriate because the electrochromic composition may comprise a plurality of different aromatic components, and the silicon-based substituents of the different aromatic components may have different types of hydrolyzable groups.

Each silicon-based substituent has at least one hydrolyzable group or a hydrolyzate of a hydrolyzable group; however, it should be appreciated that the silicon-based substituent may have a plurality of hydrolyzable groups, hydrolyzates of a hydrolyzable group, or combinations thereof. The utility of the hydrolyzable group or the hydrolyzate of the hydrolyzable group in the silicon-based group is in regard to cross-linking ability, with greater cross-linking ability associated with greater numbers of such groups present in the aromatic component. The greater cross-linking ability contributes to excellent insolubility and durability of the resulting electrochromic layer as set forth above. When the silicon-based substituent includes more than one hydrolyzable group or hydrolyzate of a hydrolyzable group, at least one Y in the general structure (I) above may be the hydrolyzable group or the hydrolyzate of the hydrolyzable group to promote excellent cross-linking potential of the electrochromic composition. If only one Y of the general structure (I) is the hydrolyzable group of the hydrolyzate or the hydrolyzable group, the remaining Y may be the monovalent aliphatic $C_1$ to $C_{10}$ group.

Specific examples of the aromatic component include, but are not limited to, those set forth below and labeled as general structures (II), (III), and (IV).

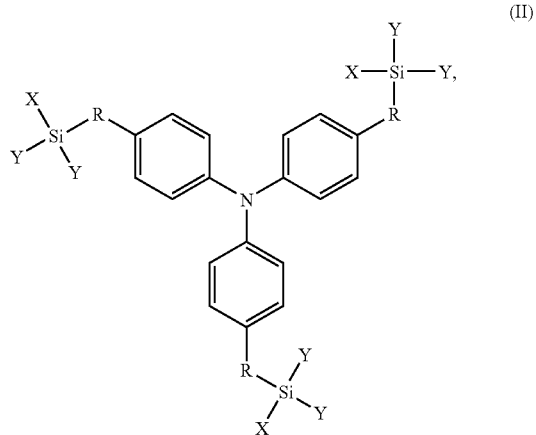

(II)

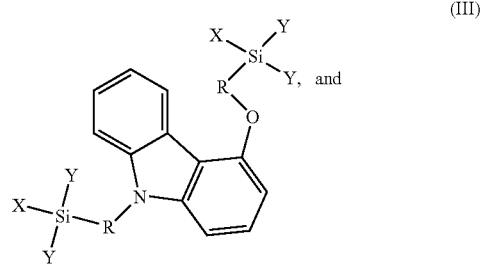

(III)

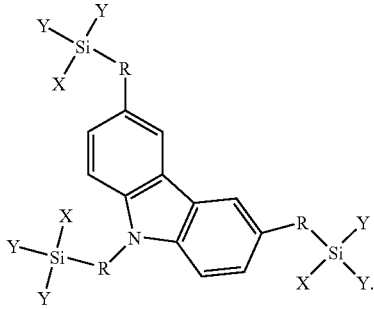

(IV)

It should be appreciated that the electrochromic composition may comprise only one aromatic component or any combination of aromatic components, such as a combination of the aromatic components represented by the general structures (II), (III), and (IV).

The electrochromic composition comprising the aromatic component may be formed by providing an aromatic group that becomes the aromatic core of the aromatic component. At least two silicon-based groups are then bonded to the aromatic group, which silicon-based groups become the silicon-based substituents that pend from the aromatic core.

In one embodiment of the present invention, the aromatic group is reacted with sodium hydroxide and an aliphatic compound having from 1 to 10 carbon atoms and further having a vinyl moiety and a halogen moiety on opposite ends of the aliphatic compound. One example of the aliphatic compound is an allyl bromide. The aliphatic compound bonds to the aromatic group and produces an acidic byproduct due to the loss of the halogen moiety. The aromatic group with the aliphatic compound bonded thereto is then reacted with a chlorosilane, such as trichlorosilane, in the presence of a catalyst, such as platinum. The chlorosilane and vinyl moiety of the aliphatic compound react, thereby saturating the aliphatic compound. This method may be repeated as desired to bond a second, third, or fourth aliphatic compound to the aromatic group and a second, third, or fourth chlorosilane group to the aliphatic compound.

In another embodiment of the present invention, the aromatic group is reacted with N-Bromosuccinimide (NBS) to form a brominated aromatic group. The brominated aromatic group is then reacted with the aliphatic compound in the presence of magnesium. The aliphatic compound bonds to the aromatic group and produces a magnesium bromide byproduct due to the loss of the halogen moiety. The aromatic group with the aliphatic compound bonded thereto is then reacted with the chlorosilane in the presence of the catalyst. The chlorosilane and the vinyl moiety of the aliphatic compound react, thereby saturating the aliphatic compound. This method may be repeated as desired to bond a second, third, or fourth aliphatic compound to the aromatic group and a second, third, or fourth trichlorosilane group to the aliphatic compound.

In one embodiment, the electrochromic composition may further comprise a branching component having a general structure (V):

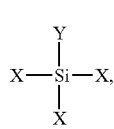

(V)

wherein X and Y are the same as set forth above. As the name suggests, the branching component may be present in the electrochromic composition to introduce cross-linking into a resulting dehydration reaction product of the hydrolyzed aromatic component and the branching component. The cross-linking introduced into the dehydration reaction product by the branching component has the same effect as cross-linking set forth above, which is to provide the electrochromic layer with excellent insolubility and durability.

In one embodiment, the electrochromic composition may further comprise, in addition to the aromatic component and, optionally, the branching component, an additional aromatic component. The additional aromatic component is different from the aromatic component and comprises an aromatic portion and a single silicon-based substituent pending from the aromatic portion.

The difference between the aromatic component and the additional aromatic component lies in the number of silicon-based substituents pending from the aromatic portion. Because the additional aromatic component only has a single silicon-based substituent pending from the aromatic portion, the resulting dehydration reaction product, when the additional aromatic component is reacted along with the aromatic component, is a polysiloxane that comprises the aromatic portion from the additional aromatic component as a pendant or terminal group in the polysiloxane. The pendant or terminal aromatic portions further contribute to the electrochromic properties of the electrochromic composition, and electrochromic layers formed therefrom.

The specific aromatic cores set forth above for the aromatic component may also be suitable for the aromatic portion of the additional aromatic component, and the single silicon-based substituent of the additional aromatic component may be bonded to the aromatic portion in the same manner as the silicon-based substituents are bonded to the aromatic cores in the aromatic component as described above. The single silicon-based substituent may be the same as the silicon-based substituents described above for the aromatic component, i.e., the single silicon-based substituent of the additional aromatic component has a silicon-bonded group selected from the group of hydrolyzable groups, hydrolyzates of a hydrolyzable group, and combinations thereof.

Specific examples of the additional aromatic component include, but are not limited to, those set forth below and labeled as general structures (VI), (VII), (VIII), (IX), and (X). It should be appreciated that the electrochromic composition may comprise only one additional aromatic component or any combination of additional aromatic components.

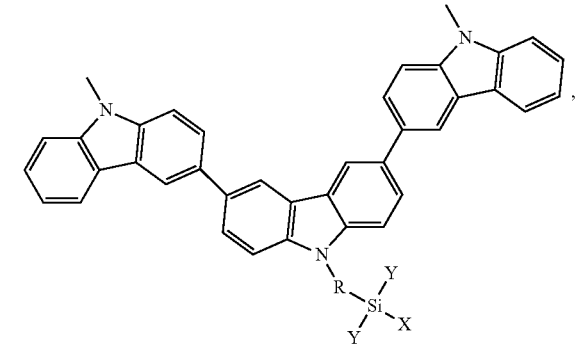

(VI)

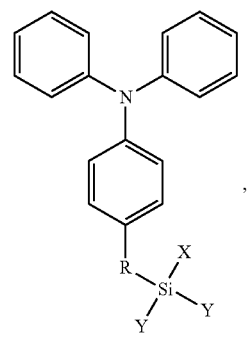

(VII)

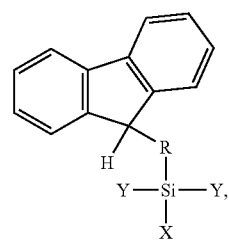

(VIII)

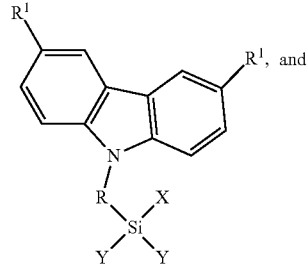

(IX)

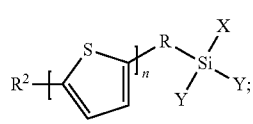

(X)

wherein X, Y, and R are the same as set forth above; and $R^1$ is selected from the group of a hydrogen atom, a methyl group, a group having the general structure (XI):

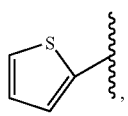

(XI)

a group having the general structure (XII):

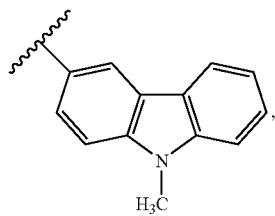

(XII)

and combinations thereof; $R^2$ is selected from the group of a hydrogen atom, a methyl group, and combinations thereof; and n is an integer of from 1 to 3.

In one embodiment, the electrochromic composition including the aromatic component and optional branching component and additional aromatic component may be provided in a form in which the hydrolyzable groups are already hydrolyzed. Alternatively the electrochromic composition may be reacted with water to hydrolyze the hydrolyzable groups present in the aromatic component and, if present, the branching component and the additional aromatic component. Prior to the reaction with water, the electrochromic composition is typically dispersed in an organic solvent. In one embodiment of the present invention, the organic solvent is a ketone, e.g. methyl isobutyl ketone, though any suitable organic solvent known by those skilled in the art may be utilized. The organic solvent may act as a carrier for the electrochromic composition and is typically unreactive. The reaction with water is a hydrolysis reaction; i.e., the water reacts with the hydrolyzable groups bonded to the silicon-based group in the aromatic component, branching component, and additional aromatic component to form hydrolyzates of hydrolyzable groups. In one embodiment of the present invention, when the hydrolyzable group of the silicon-bonded group is a halogen, there is an acidic byproduct, e.g. hydrobromic acid, as the halogen groups are replaced with hydroxyl groups. The acidic byproduct may be rinsed from the solution of the electrochromic composition and water with additional water prior to depositing the electrochromic layer onto the first or second electrode layer. Due to natural evaporation of water from the solution, the aromatic component and optional branching component and additional aromatic component may form small numbers of siloxane bonds with each other, thereby forming an oligomer that is still liquid, prior to completing a dehydration reaction to produce the solid polysiloxane that forms the electrochromic layer.

The electrochromic composition has excellent processability, which is correlated to an average size of species in the electrochromic composition. Species, as used herein, are the individual components and partial reaction products thereof that are present in the electrochromic composition prior to further processing steps involving the removal of water. Electrochromic compositions having an average species size of less than or equal to about 1 micron have excellent processability. Average species size is measured by passing the electrochromic composition through a filter.

The electrochromic layer is typically formed on the first or second electrode layer by depositing the solution including the electrochromic composition and water through spinning, spraying, printing, chemical vapor depositing, physical vapor depositing, or through other method known to those skilled in the art. The solution in the electrochromic layer cures to form the polysiloxane during a dehydration reaction. More specifically, the silicon-bonded hydrolyzates of the hydrolyzable groups, upon the dehydration reaction, form polysiloxane bonds (Si—O—Si), with water as a byproduct. The removal of water from the electrochromic layer drives the dehydration reaction. To remove the water from the electrochromic layer, the water may be allowed to evaporate from the solution after the electrochromic layer has been formed on the first or second electrode layer from the solution, thereby driving the dehydration reaction and forming the polysiloxane. Alternatively, the electrochromic layer may be heated after forming the electrochromic layer on the first or second electrode layer from the solution, thereby driving the dehydration reaction and forming the polysiloxane. Typically, the dehydration reaction is achieved by heating the electrochromic layer formed from the solution at a temperature of from 150 to 300° C., more typically from 165 to 250° C., most typically from 180 to 200° C. The electrochromic layer may be heated for a time of from one to ten minutes, more typically from two and a half to eight minutes, most typically from four to six minutes.

As set forth above, the polysiloxane may or may not be cross-linked, depending upon the specific aromatic component used, and further depending upon whether or not the branching component is included in the electrochromic composition. One non-limiting example of a portion of a cross-linked polysiloxane, formed when the branching component is included in the electrochromic composition, can be seen in general structure (XIII).

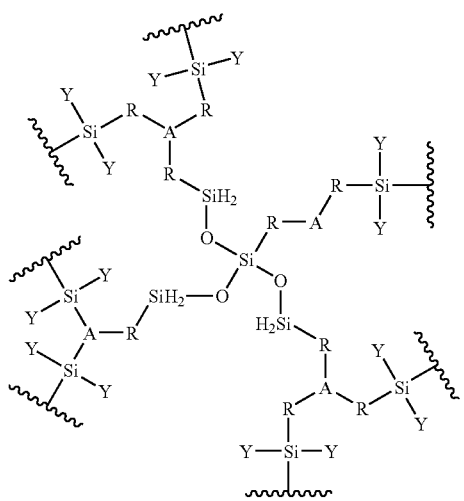

(XIII)

wherein A is the aromatic core from the aromatic component; Y and R are the same as set forth above; and wherein the cleaved bond signifies a bond from the respective silicon atom to an oxygen atom of another aromatic component, branching component, or additional aromatic component. Further, because Y can be the same as X, Y in the above structure may represent another cleaved bond from the respective silicon atom to an oxygen atom of another aromatic component. It should be appreciated that general structure (XIII) is a non-limiting example and may not actually exist in the actual cross-linked polysiloxane; the structure of the actual cross-linked polysiloxane is contingent on the aromatic component utilized and whether the branching component and the additional aromatic component are present in the electrochromic composition, and the relative amounts of each of those components.

The electrochromic layer is typically formed on the first or second electrode layer at a thickness of from about 1 to about 1,000 nanometers, more typically from about 100 to about 500 nanometers. Such thicknesses may be smaller than thicknesses of comparable electrochromic layers that achieve similar electrochromic properties as the electrochromic layer of the present invention. In fact, the thickness of the electrochromic layer may be minimized while still achieving desirable electrochromic properties that are typically characteristic of thicker electrochromic layers. Further, the change in light transmission properties of the electrochromic layer may be customized depending on the aromatic components utilized within the electrochromic layer, e.g. a particular color may be achieved when specific aromatic components are present in the electrochromic layer. The excellent compatibility of the aromatic component, the additional aromatic component and the optional branching component allow for the electrochromic composition to be easily customized due to minimized processability and formation requirements of the electrochromic composition.

The following examples, illustrating the method of forming the electrochromic composition of the present invention, are intended to illustrate and not to limit the invention.

EXAMPLES

To 250 mL dry THF were added 3-bromo-9-methylcarbazole (21.4 g, 82.5 mmol), 3,6-bis(ethylene boronato)-9-allylcarbazole (13.0 g, 37.5 mmol), and Aliquat 336 (7.0 g, 20% (w/w) of the monomer mass). This solution, along with aqueous $K_2CO_3$ (2 M, 94 mL, 188 mmol) and 100 mL dry THF were deoxygenated with bubbling argon for sixty minutes. Then, tetrakis(triphenylphosphine)palladium was dissolved using the dry THF. The $K_2CO_3$ solution was added via cannula immediately followed by addition of the palladium catalyst solution. The resulting solution was brought to reflux and maintained as such with stirring for three days. Then, the solution was cooled to room temperature and the aqueous phase was removed. Solvent was removed from the organic phase and the residue was purified by column chromatography on silica gel. Elution with hexanes and methylene chloride in ratios from 5:1 to 3:1 gave 3,6-bis(9-methylcarbazol-3-yl)-9-allylcarbazole with a yield of about 7.5 g, at a concentration of about 38% by weight. 1H NMR (CDCl3) δ 8.55 (d, 2 H, J=1.5 Hz); 8.47 (d, 2 H, J=1.5 Hz); 7.88 (dt, 4 H, J=8.4, 1.8 Hz); 7.48 (m, 8 H); 7.29 (m, 2 H); 6.10 (m, 1 H); 5.25 (d, 1 H, J=10.2 Hz); 5.15 (d, 1 H, J=17.7 Hz); 3.88 (s, 6 H).

To a three-neck flask fitted with a reflux condenser and a dropping funnel were added the 3,6-bis(9-methylcarbazol-3-yl)-9-allylcarbazole (10 g), anhydrous THF (100 g), and platinum (0) 1,3-divinyl-1,1,3,3-tetramethyldisiloxane complex (250 mg of a 0.05% solution in anhydrous toluene). Then, trichlorosilane (30 g) was slowly added. When the addition of trichlorosilane was completed, the mixture was heated to 60° C. and maintained at that temperature for two hours. Then, the mixture was distilled at 0.02 torr to remove volatiles and gave 9-(3-trichlorosilylprop-1-yl)carbazole with a yield of about 5.6 g, at a concentration of about 90% by weight. 1 H NMR (CDCl3) δ 8.53 (d, 2 H, J=1.5 Hz); 8.46 (d, 2 H, J=1.2 Hz); 8.21 (d, 2 H, J=7.8 Hz); 7.87 (m, 4 H); 7.48 (m, 8 H); 7.27 (m, 2 H); 6.10 (m, 1 H); 5.40 (d, 1 H, J=9.0 Hz); 5.14 (d, 1 H, J=15.9 Hz); 5.00 (m, 2 H); 3.91 (s, 6 H).

To a one-neck flask was added the 9-(3-trichlorosilylprop-1-yl)carbazole (7.4 g), N,N-diphenyl-4-(3-trichlorosilyl-prop-1-yl)aniline (12.6 g) and methyl isobutyl ketone (250 g). Then, silicon tetrachloride (1.6 g) and 4-(trichlorosilylprop-1-oxy)-9-(3-trichlorosilylprop-1-yl)carbazole (2.4 g) were added. The resulting solution was cooled at −78° C. for one hour. Next, water (10 g) was added over the course of one hour. When the addition of water was complete, the solution was allowed to slowly warm to room temperature. After this time, the solution was washed with water until the washings were no longer acidic. Residual water was removed in vacuo and the solution was filtered using a 0.1 μm PTFE syringe filter to produce an electrochromic composition.

ITO/glass slides were cleaned using a nylon brush and a 1% Alconox solution. Then, the slides were sonicated for ten minutes each in a 1% Alconox solution, deionized water, isopropanol, and toluene. The slides were then briefly dried in an oven at 150° C. After that, the slides were subjected to an oxygen plasma for five minutes. The electrochromic composition was used to spin-coated onto the substrates to form an electrochromic layer. Then, about 5 mm was removed from one edge of the electrochromic layer by wiping with a toluene-soaked cotton swab. The electrochromic layer was then cured at 190° C. for thirty minutes on a hot plate. Thickness measurements were obtained using a KLH-Tencor Alpha Step profilometer to determine the height difference between the electrochromic layer and the bare substrate. Then, the spin-coating procedure was repeated using pure solvent in place of the electrochromic composition. The electrochromic layers were briefly dried in an oven at 100° C. and the thickness measurements were repeated. The ratio between the thickness of the electrochromic layers before and after the solvent rinses was taken as a measure of solvent resistance. The electrochromic layers here showed thickness ratios of at least ninety percent.

CV measurements were obtained using a PAR 263a potentiostat and PowerSuite software. The working electrode was an ITO/glass slide. HIM CV experiments were performed using a cured electrochromic layer with a thickness of 30 nm deposited on the ITO/glass slide. The auxiliary electrode was a platinum wire, and the quasi-reference electrode was a non-aqueous Ag/Ag+ reference electrode. The electrolyte solution was 0.1 M tetrabutylammonium tetrafluoroborate in acetonitrile. All CV data was obtained by cycling the applied bias between zero and one volt relative to the reference electrode. The electrochromic layer showed a transmissive neutral state and an opaque blue oxidized state. The transition between states occurred in the range of 500 to 800 mV versus the reference electrode. The electrochromic layer was found to be bistable. The electrochromic layers were switched between their neutral and oxidized states several hundred times with no apparent degradation in performance.

The present invention has been described herein in an illustrative manner, and it is to be understood that the terminology which has been used is intended to be in the nature of words of description rather than of limitation. Obviously, many modifications and variations of the present invention are possible in light of the above teachings. The invention may be practiced otherwise than as specifically described within the scope of the appended claims.

What is claimed is:

1. An electrochromic composition comprising an aromatic component having:
   an aromatic core; and
   at least two silicon-based substituents pending from said aromatic core, said silicon-based substituents having a silicon-bonded group selected from the group of hydrolyzable groups, hydrolyzates of a hydrolyzable group, and combinations thereof.

2. An electrochromic composition as set forth in claim 1, wherein said aromatic core is selected from the group of aromatic amines, aromatic thiols, aromatic ethers, and combinations thereof.

3. An electrochromic composition as set forth in claim 1, wherein said aromatic core comprises a polyaromatic component.

4. An electrochromic composition as set forth in claim 1, wherein at least one of said silicon-based substituents has more than one silicon-bonded group selected from the group of hydrolyzable groups, hydrolyzates of a hydrolyzable group, and combinations thereof.

5. An electrochromic composition as set forth in claim 1, wherein said silicon-based substituents are represented by the general formula:

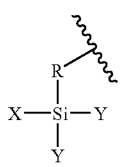
(I)

wherein:
   X is selected from the group of hydrolyzable groups, hydrolyzates of a hydrolyzable group, and combinations thereof;
   Y is selected from the group of X, monovalent aliphatic $C_1$ to $C_{10}$ groups, phenyl groups, and combinations thereof; and
   R is a divalent aliphatic group having from 0 to 10 carbon atoms, wherein R is bonded to said aromatic core.

6. An electrochromic composition as set forth in claim 1, wherein said aromatic component is selected from the group of:

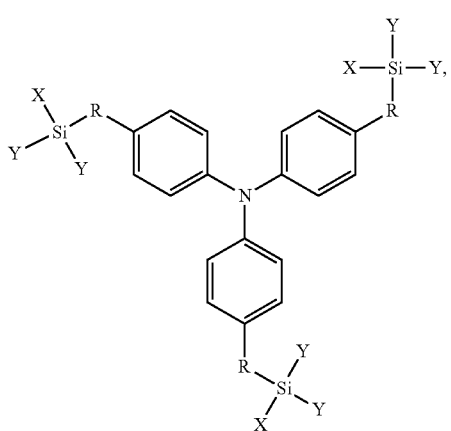
(II)

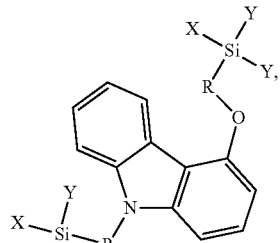
(III)

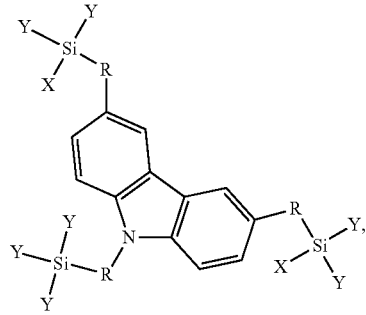
(IV)

and combinations thereof.

7. An electrochromic composition as set forth in claim 1 further comprising at least one branching component having the general formula:

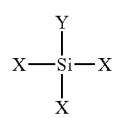
(V)

wherein:
   X is selected from the group of hydrolyzable groups, hydrolyzates of a hydrolyzable group, and combinations thereof; and
   Y is selected from the group of X, monovalent aliphatic $C_1$ to $C_{10}$ groups, phenyl groups, and combinations thereof.

8. An electrochromic composition as set forth in claim 1 further comprising an additional aromatic component having:
   an aromatic portion; and
   a single silicon-based substituent pending from said aromatic portion, wherein said single silicon-based substituent has a silicon-bonded group selected from the group of hydrolyzable groups, hydrolyzates of a hydrolyzable group, and combinations thereof.

9. An electrochromic composition as set forth in claim 8, wherein said aromatic portion is selected from the group of aromatic amines, aromatic thiols, aromatic ethers, and combinations thereof.

10. An electrochromic composition as set forth in claim 8, wherein said aromatic portion comprises a polyaromatic component.

11. An electrochromic composition as set forth in claim 8, wherein said single silicon-based substituent has more than one silicon-bonded group selected from the group of hydrolyzable groups, hydrolyzates of a hydrolyzable group, and combinations thereof.

12. An electrochromic composition as set forth in claim 8, wherein said at least one additional aromatic component is selected from the group of:

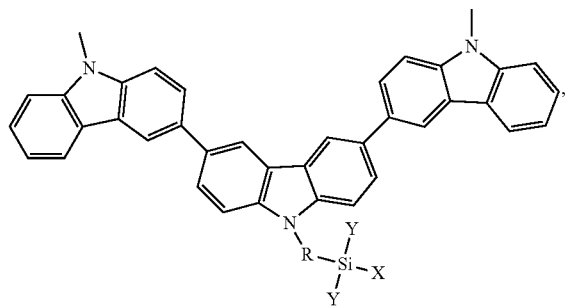

(VI)

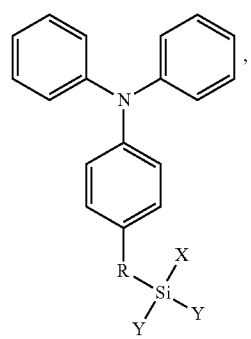

(VII)

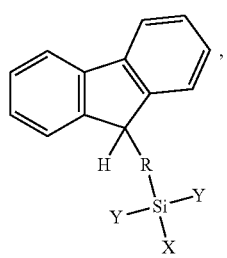

(VIII)

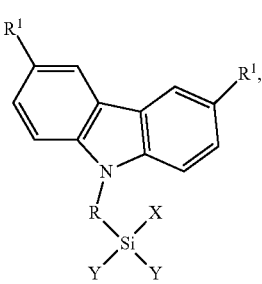

(IX)

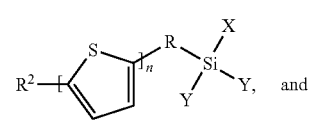

and combinations thereof, wherein:

X is selected from the group of hydrolyzable groups, hydrolyzates of a hydrolyzable group, and combinations thereof;

Y is selected from the group of X, monovalent aliphatic $C_1$ to $C_{10}$ groups, phenyl groups, and combinations thereof;

R is a divalent aliphatic group having from 0 to 10 carbon atoms;

$R^1$ is selected from the group of a hydrogen atom, a methyl group, a group having the structure:

(XI)

a group having the structure:

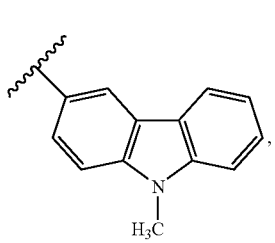

(XII)

and combinations thereof;

$R^2$ is selected from the group of a hydrogen atom, a methyl group, and combinations thereof; and n is an integer of from 1 to 3.

13. An electrochromic composition as set forth in claim 1 having an average species size of less than or equal to about 1 micron.

14. A method of forming an electrochromic composition comprising the steps of:
providing an aromatic group;
bonding at least two silicon-based groups to the aromatic group;
the at least two pendent silicon-based groups having a silicon-bonded group selected from the group of hydrolyzable groups, hydrolyzates of a hydrolyzable group, and combinations thereof.

15. A method as set forth in claim 14, wherein the aromatic group is selected from the group of aromatic amines, aromatic thiols, aromatic ethers, and combinations thereof.

16. A method as set forth in claim 14, wherein the aromatic group comprises a polyaromatic component.

17. A method as set forth in claim 14, wherein at least one of the at least two silicon-based groups has more than one silicon-bonded group selected from the group of hydrolyzable groups, hydrolyzates of a hydrolyzable group, and combinations thereof.

18. An electrochromic apparatus comprising:
a first electrode layer;
a second electrode layer spaced from and disposed substantially parallel to said first electrode layer;
an electrochromic layer disposed between said first and second electrode layers, said electrochromic layer comprising the dehydration reaction product of a hydrolyzed aromatic component having an aromatic core and at least two silicon-based substituents pending from said aromatic core, said silicon-based substituents having a silicon-bonded hydrolyzate of a hydrolyzable group; and an electrolyte layer disposed between said electrochromic layer and said first electrode layer.

19. An electrochromic apparatus as set forth in claim 18, wherein said aromatic core is selected from the group of aromatic amines, aromatic thiols, aromatic ethers, and combinations thereof.

20. An electrochromic composition as set forth in claim 18, wherein said aromatic core comprises a polyaromatic component.

21. An electrochromic apparatus as set forth in claim 18, wherein said electrochromic layer further comprises the dehydration reaction product of an additional aromatic component comprising an aromatic portion having a single silicon-based substituent pending from said aromatic portion, wherein said single silicon-based substituent has a silicon-bonded hydrolyzate of a hydrolyzable group.

22. An electrochromic apparatus as set forth in claim 18, wherein said electrochromic layer further comprises the dehydration reaction product of at least one branching component having the general formula:

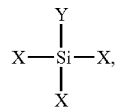

(XIII)

wherein:
X is a hydrolyzate of a hydrolyzable group; and
Y is selected from the group of X, monovalent aliphatic $C_1$ to $C_{10}$ groups, phenyl groups, and combinations thereof.

23. An electrochromic apparatus as set forth in claim 18 further comprising a first substrate layer disposed on an exterior face of one of said electrode layers opposite said electrolyte layer.

24. An electrochromic apparatus as set forth in claim 23 further comprising a second substrate layer disposed on an exterior face of the other of said electrode layers opposite said electrochromic layer.

25. An electrochromic apparatus as set forth in claim 18, wherein said electrolyte layer comprises a liquid electrolyte.

* * * * *